(12) United States Patent
Goldberg et al.

(10) Patent No.: US 12,108,988 B2
(45) Date of Patent: Oct. 8, 2024

(54) SYSTEM AND METHOD FOR MEASURING PUPILLARY DISTANCE AND USES THEREOF

(71) Applicant: Warby Parker Inc., New York, NY (US)

(72) Inventors: Dee Celeste Goldberg, New York, NY (US); Benjamin Cohen, New York, NY (US); Taylor Alexandra Duffy, Waldwick, NJ (US)

(73) Assignee: Warby Parker Inc., New York, NY (US)

( * ) Notice: Subject to any disclaimer, the term of this patent is extended or adjusted under 35 U.S.C. 154(b) by 531 days.

(21) Appl. No.: 17/345,876

(22) Filed: Jun. 11, 2021

(65) Prior Publication Data

US 2021/0393121 A1 Dec. 23, 2021

Related U.S. Application Data

(60) Provisional application No. 63/040,184, filed on Jun. 17, 2020.

(51) Int. Cl.
*A61B 3/11* (2006.01)
*G06T 17/20* (2006.01)

(52) U.S. Cl.
CPC ............... *A61B 3/11* (2013.01); *G06T 17/20* (2013.01); *G06T 2210/41* (2013.01)

(58) Field of Classification Search
CPC ........ A61B 3/11; G06T 17/20; G06T 2210/41
USPC ....................................................... 351/204
See application file for complete search history.

(56) References Cited

U.S. PATENT DOCUMENTS

| | | |
|---|---|---|
| 2,818,775 A | 1/1958 | Ullrich |
| 4,007,990 A | 2/1977 | McDevitt, Jr. et al. |
| 4,070,115 A | 1/1978 | Humphrey |
| 4,090,790 A | 5/1978 | Dragon et al. |
| 4,779,979 A | 10/1988 | Iwane |
| 5,231,674 A | 7/1993 | Cleveland et al. |
| 5,247,341 A | 9/1993 | Kurachi et al. |

(Continued)

FOREIGN PATENT DOCUMENTS

| | | |
|---|---|---|
| DE | 19632829 A1 | 3/1997 |
| DE | 102007057260 A1 | 6/2009 |

(Continued)

OTHER PUBLICATIONS

Aug. 11, 2017 International Search Report and Written Opinion of the ISA for PCT International Application No. PCT/US2017/033064.

(Continued)

*Primary Examiner* — William R Alexander
*Assistant Examiner* — Sharrief I Broome
(74) *Attorney, Agent, or Firm* — Duane Morris LLP

(57) ABSTRACT

A method of operating a pupillary distance system is disclosed. The method comprises the steps of capturing, with at least one camera of the pupillary distance system a 2D image and a corresponding 3D depth map of a face of a subject. A determination of pupil localization information is made using the 2D image and corresponding 3D depth map. The pupil location is further refined based on the pupil localization information. Pupil center coordinates are determined and the pupillary distance is calculated for a subject between centers of each pupil. Processes and uses thereof are also disclosed.

17 Claims, 13 Drawing Sheets

(56) References Cited

U.S. PATENT DOCUMENTS

| | | | |
|---|---|---|---|
| 5,307,141 A | 4/1994 | Fujieda | |
| 5,379,111 A | 1/1995 | Kajino et al. | |
| 5,414,505 A | 5/1995 | Ikezawa et al. | |
| 5,489,978 A | 2/1996 | Okumura et al. | |
| 5,521,700 A | 5/1996 | Kajino et al. | |
| 5,621,564 A | 4/1997 | Kageyama et al. | |
| 5,657,710 A | 8/1997 | Foster et al. | |
| 5,682,234 A | 10/1997 | Kajino | |
| 5,684,576 A | 11/1997 | Kajino et al. | |
| 5,855,074 A | 1/1999 | Abitbol et al. | |
| 6,056,633 A | 5/2000 | Seseña et al. | |
| 6,496,253 B1 | 12/2002 | Vokhmin | |
| 6,621,564 B2 | 9/2003 | Akiyama et al. | |
| 6,657,710 B2 | 12/2003 | Kajino et al. | |
| 6,972,837 B2 | 12/2005 | Kajino | |
| 7,209,224 B2 | 4/2007 | Kajino | |
| 7,245,362 B2 | 7/2007 | Kobayashi et al. | |
| 7,609,371 B2 | 10/2009 | Kajino | |
| 7,733,468 B2 | 6/2010 | Kajino | |
| 7,742,158 B2 | 6/2010 | Divo et al. | |
| 8,789,945 B2 | 7/2014 | Suzaki et al. | |
| 9,019,485 B2 | 4/2015 | Ignatovich et al. | |
| 9,228,920 B2 | 1/2016 | Blonde et al. | |
| 9,549,669 B2 | 1/2017 | Limon | |
| 9,778,136 B2 | 3/2017 | Suzuki et al. | |
| 10,036,685 B2 | 7/2018 | Goldberg et al. | |
| 10,321,820 B1 | 6/2019 | Gollier et al. | |
| 10,330,566 B2 | 6/2019 | Hofmann et al. | |
| 2012/0105799 A1 | 5/2012 | Stewart | |
| 2013/0088490 A1 | 4/2013 | Rasmussen et al. | |
| 2016/0223429 A1 | 8/2016 | Fecnher et al. | |
| 2016/0299360 A1 | 10/2016 | Fonte et al. | |
| 2017/0076523 A1 | 3/2017 | Rumble et al. | |
| 2017/0079523 A1 | 3/2017 | Limon | |
| 2017/0322110 A1 | 11/2017 | Conrad et al. | |
| 2017/0336654 A1* | 11/2017 | Seitz | G02C 13/005 |
| 2018/0120198 A1 | 5/2018 | Glasenapp et al. | |
| 2018/0224675 A1 | 8/2018 | Gueu et al. | |
| 2018/0268458 A1 | 9/2018 | Popa et al. | |
| 2019/0033624 A1* | 1/2019 | Breuninger | G02C 13/005 |
| 2019/0072455 A1 | 3/2019 | Limon et al. | |
| 2020/0242800 A1* | 7/2020 | Chen | G06V 40/171 |
| 2021/0012525 A1* | 1/2021 | Barton | G06V 40/171 |

FOREIGN PATENT DOCUMENTS

| | | |
|---|---|---|
| EP | 0558015 B1 | 9/1993 |
| GB | 1042954 A | 9/1966 |
| WO | WO 2016/076530 A1 | 5/2016 |
| WO | WO 2016/181308 A1 | 11/2016 |
| WO | WO 2016/181309 A1 | 11/2016 |
| WO | WO 2016/181310 A1 | 11/2016 |
| WO | WO 2017/125902 A1 | 7/2017 |
| WO | WO 2021/041386 A1 | 3/2021 |

OTHER PUBLICATIONS

Jan. 22, 2020 International Search Report and the Written Opinion of the ISA for PCT International Application No. PCT/US2019/056827.

Nov. 23, 2020 International Search Report and the Written Opinion of the ISA for PCT International Application No. PCT/US2020/47757.

Extended European Search Report for corresponding European Patent Application No. 21824796.3 issued Jun. 17, 2024, 8 pages.

* cited by examiner

SYSTEM AND METHOD FOR MEASURING PUPILLARY DISTANCE AND USES THEREOF

CROSS-REFERENCE TO RELATED APPLICATIONS

This application claims the benefit of and priority in and to U.S. Ser. No. 63/040,184, filed Jun. 17, 2020, which is hereby incorporated by reference in its entirety.

FIELD

The present disclosure generally relates to the technical field of optometry. More specifically, the present disclosure is directed to systems and methods for measuring pupillary distance and uses thereof.

BACKGROUND

The following includes information that may be useful in understanding the invention. It is not an admission that any of the information specifically or implicitly referenced herein is prior art, or essential, to the described or claimed invention. All patents, patent applications, publications and products mentioned herein are hereby incorporated by reference in their entirety.

Pupillary distance ("PD") is the distance between pupils of a subject, such as a human. The accuracy of this distance is a determining factor in the comfort and fit of eyeglasses, sunglasses or virtual reality headsets. Mismeasured PD can lead to lenses with prismatic effects that cause headaches, blurry vision, eyestrain, nausea, vertigo, dizziness, disorientation and other issues to the subject. Traditionally, PD measurement is absent from eyeglasses or sunglasses prescriptions, but it is required for fulfilling custom prescription eyeglass or sunglass orders. The average PD for an adult human is about 63 mm. However, the PD measurement can vary widely between 51 mm and 74.5 mm for women and 53 mm and 77 mm for men. PD is critical when fitting eyeglasses or sunglasses with progressive lenses because a precise lens-to-pupil alignment is required to ensure comfortable vision at all distances.

Currently, there are various ways to measure PD. For example, there are two primary methods for PD measurement: single PD and dual PD. Single PD (or binocular PD) is the measurement from pupil to pupil between each eye. Dual PD (or monocular PD) is the measurement from your nose bridge to each eye.

Traditional ways of obtaining a PD measurement may include using a ruler. For this type of measurement, a subject is required to stand approximately 8 inches from a mirror and a ruler is aligned on one eye pupil across the subject's brow to the other pupil to obtain a PD measurement. This type of measurement is inaccurate because the contours of the face and alignment of the ruler may vary.

A subject may obtain his/her PD measurement with assistance of another individual, possibly in a commercial setting. In this example, the PD may be measured using a corneal reflection pupillometer. Alternatively, e-commerce customers may submit a photo of their face while holding a standard size reference (e.g., a credit card, etc.), and the photo may be processed remotely to obtain the PD.

Each of the traditional examples described above are cumbersome and/or resource-intensive ways of obtaining a PD measurement. Also, certain traditional examples, such as using a corneal reflection pupillometer, may require the subject to be less than 6 feet apart from the person making the measurement, causing them to violate social distancing rules during a pandemic, such as COVID-19. Further, corneal reflection pupillometers are not always reliable measures of PD since they are subject to human error and can be miscalibrated. Because the PD is required for fulfilling custom prescription eyeglass or sunglass orders, developing a seamless, convenient and contactless way to obtain a PD measurement enhances the consumer experience. Furthermore, developing easier and more accurate ways to obtain a PD measurement promotes e-commerce and expands consumer options in obtaining comfortable and accurate eyewear. Finally, retailers may use image and and/or statistical information relating to PD measurements to improve manufacturing processes and/or provide eyewear recommendations based on user satisfaction and purchase history correlated with PD measurements.

Thus, there is a need to develop an improved system or method for measuring PD that will increase accuracy, efficiency, reliability, convenience and use, while decreasing or eliminating human intervention and/or human error.

SUMMARY

The invention described and claimed herein has many attributes and aspects including, but not limited to, those set forth or described or referenced in this Summary. It is not intended to be all-inclusive and the invention described and claimed herein are not limited to or by the features or embodiments identified in this Summary, which is included for purposes of illustration only and not restriction.

In various embodiments of the present disclosure, systems and methods are provided that obtain and use a succession of image processing algorithms to localize pupils in a two-dimensional ("2D") image. The pupils are then localized in world coordinates using three-dimensional ("3D") data provided by a depth sensing image. Using the world coordinates, the physical distance between pupils may be computed. The systems and methods described herein advantageously provide for an accurate and more convenient way of obtaining a PD measurement. Furthermore, the PD measurement obtained may be used for eyeglasses (or spectacles), sunglasses, virtual reality headsets, goggles, safety eyewear, smartglasses (including, but not limited to, augmented reality eyeglasses) and other eyewear. Finally, facial measurements for a subject, to include PD, may be associated with a user account such that product recommendations may be provided based on a user's facial measurements and historical customer satisfaction data and purchase history associated with facial measurements.

In various embodiments of the present disclosure, the systems and methods described herein can obtain facial measurements for use in a virtual fitting or try-on system or application. In some embodiments, a virtual fitting or try-on system can provide a user with an interface to try on and/or purchase a pair of eyeglasses or sunglasses virtually using facial measurements, including PD measurements, obtained from the disclosure described herein. The systems and methods described herein, when incorporated into a virtual fitting or try-on system, improve the user's e-commerce experience since it allows the user to try-on virtually potential eyeglasses or sunglasses, obtain a PD measurement, and select and purchase custom prescription eyeglasses or sunglasses online, and without the need to visit a physical store. The systems and methods described herein also improves virtual fitting or try-on systems by obtaining and storing additional facial measurements that can lead to better product recommendations. The systems and methods of the present disclosure may advantageously interface with the virtual try-on system and method described in U.S. patent application Ser. No. 16/550,614, filed Aug. 26, 2019 (entitled "Virtual Fitting Systems and Methods for Spectacles"). In various embodiments of the present disclosure, a method of operating a pupillary distance system is described. In some embodiments, the method comprises the steps of capturing, with at least one camera of the pupillary distance system, a first 2D image and a corresponding 3D depth map of a face of a subject; determining pupil localization information using the first 2D image and corresponding 3D depth map; refining one or more pupil locations based on the pupil localization information; determining one or more pupil center coordinates; and calculating the PD of the subject between centers of each pupil.

In some embodiments of the present disclosure, the pupil localization information is determined using a plurality of face mesh landmarks to generate a plurality of face mesh vertices near the center of an eye opening to obtain one or more initial pupil locations on the subject.

In some embodiments of the present disclosure, the one or more pupil locations are refined using a convolution with one or more kernels and one or more 2D center-surround filters. In some embodiments, the one or more kernels use a pupil estimate size of approximately 12 mm.

In some embodiments of the present disclosure, calculating the PD uses depth map values that correspond to the refined one or more pupil locations in the 2D image.

In some embodiments of the present disclosure, the PD is determined by using points on a 3D face mesh that correspond to the centers of each pupil.

In some embodiments of the present disclosure, the method further comprising the steps of performing a correction on the PD calculated using a distance that the first 2D image is taken from the at least one camera.

In various embodiments of the present disclosure, a non-transitory computer readable medium having computer-executable instructions embodied thereon is provided. The computer-executable instructions when executed by a processor, the computer-executable instructions cause the processor to: obtain, from at least one camera, a first 2D image and a corresponding 3D depth map of a face of a subject; determine pupil localization information using the first 2D image and corresponding 3D depth map; refine one or more pupil locations based on the pupil localization information; determine one or more pupil center coordinates; and calculate the PD of the subject between centers of each pupil.

In some embodiments of the present disclosure, the pupil localization information is determined using a plurality of face mesh landmarks to generate a plurality of face mesh vertices near the center of an eye opening to obtain one or more initial pupil locations of the subject.

In some embodiments of the present disclosure, the one or more pupil locations are refined using a convolution with one or more kernels and one or more 2D center-surround filters. In some embodiments, the one or more kernels use a pupil estimate size of approximately 12 mm.

In some embodiments of the present disclosure, calculating the PD uses depth map values that correspond to the refined one or more pupil locations in the 2D image.

In some embodiments of the present disclosure, calculating the PD is determined by using points on a 3D face mesh that correspond to the centers of each pupil.

In some embodiments of the present disclosure, the computer-executable instructions further cause the processor to perform a correction on the PD calculated using a distance that the first 2D image is taken from the at least one camera.

In various embodiments of the present disclosure, a pupillary distance system is provided, comprising one or more mobile devices. In some embodiments, the one or more mobile devices includes a mobile device comprising at least one camera, memory storing information associated with images and information obtained from the at least one camera, and a processor. The processor is configured to: obtain, from the at least one camera, a 2D image and a corresponding 3D depth map of a face of a subject; determine pupil localization information using the 2D image and corresponding 3D depth map; refine one or more pupil locations based on the pupil localization information; determine one or more pupil center coordinates; and calculate the PD between centers of each pupil of the subject.

In some embodiments of the present disclosure, the pupil localization is determined using a plurality of face mesh landmarks to generate a plurality of face mesh vertices near the center of an eye opening to obtain one or more initial pupil locations of the subject.

In some embodiments of the present disclosure, the one or more pupil locations are refined using a convolution with one or more kernels and one or more 2D center-surround filters. In some embodiments, the one or more kernels use a pupil estimate size of approximately 12 mm.

In some embodiments of the present disclosure, calculating the PD uses depth map values that correspond to the refined one or more pupil locations in the 2D image.

In some embodiments of the present disclosure, calculating the PD is determined by using points on a 3D face mesh that correspond to the centers of each pupil.

In some embodiments of the present disclosure, performing a correction on the PD calculated using a distance that the first 2D image is taken from the at least one camera.

BRIEF DESCRIPTION OF THE FIGURES

The accompanying drawings, which are incorporated herein and form a part of the specification, illustrate the aspects of the present disclosure and, together with the description, further serve to explain the principles of the aspects and to enable a person skilled in the pertinent art to make and use the aspects. The drawings are for illustration purposes only, show exemplary non-limiting embodiments, and are not necessarily drawn to scale.

FIG. 4A shows a filter kernel (or kernel) with center-surround structure; FIG. 4B shows an image patch with a circle 990 with a cross symbol illustrating the location with the maximum response to the kernel; and FIG. 4C shows an image response to convolution with the kernel.

In FIG. 5, the solid-lined circle 2000 indicates the initial estimate of the iris boundary; the solid cross symbol 2001 indicates the initial estimate for the iris center; the closed dots 3010 indicate inlier boundary points; the open dots 3020 indicate outlier boundary points; the dotted-lined circle 3000 indicates the final estimate for iris boundary; and the dotted cross symbol 3001 indicates the final estimate for iris center.

DETAILED DESCRIPTION

This description of the exemplary embodiments is intended to be read in connection with the accompanying drawings, which are to be considered part of the entire written description. The use of the singular includes the plural unless specifically stated otherwise. The use of "or" means "and/or" unless stated otherwise. Furthermore, the use of the term "including," as well as other forms such as "includes" and "included," is not limiting. In addition, terms such as "element" or "component" encompass both elements and components comprising one unit, and elements and components that comprise more than one subunit, unless specifically stated otherwise. Additionally, the section headings used herein are for organizational purposes only, and are not to be construed as limiting the subject matter described.

The following description is provided as an enabling teaching of a representative set of examples. Many changes can be made to the embodiments described herein while still obtaining beneficial results. Some of the desired benefits discussed below can be obtained by selecting some of the features discussed herein without utilizing other features. Accordingly, many modifications and adaptations, as well as subsets of the features described herein are possible and can even be desirable in certain circumstances. Thus, the following description is provided as illustrative and is not limiting.

As used herein, use of a singular article such as "a," "an" and "the" is not intended to exclude pluralities of the article's object unless the context clearly and unambiguously dictates otherwise.

A system and method are provided in the present disclosure for determining the PD of a subject. The subject is mammal or human, and wherein the mammal or human is male, female, non-binary mammal or human (or other gender identity), adult or child. As discussed throughout this specification, the system and method advantageously provide accurate and efficient real time facial measurements for a subject. The system and method advantageously provides users with facial measurements that may be stored in an account associated with the respective user enabling the user to receive product recommendations based on facial measurements and/or consumer satisfaction data and/or purchase history associated with historical facial measurements. Such users are human, wherein human is male, female, non-binary human (or other gender identity), adult or child. Finally, the system and method may advantageously use consumer satisfaction data to improve facial measurement calculations using artificial intelligence, such as machine learning and deep learning.

System Overview

Figure 1A:
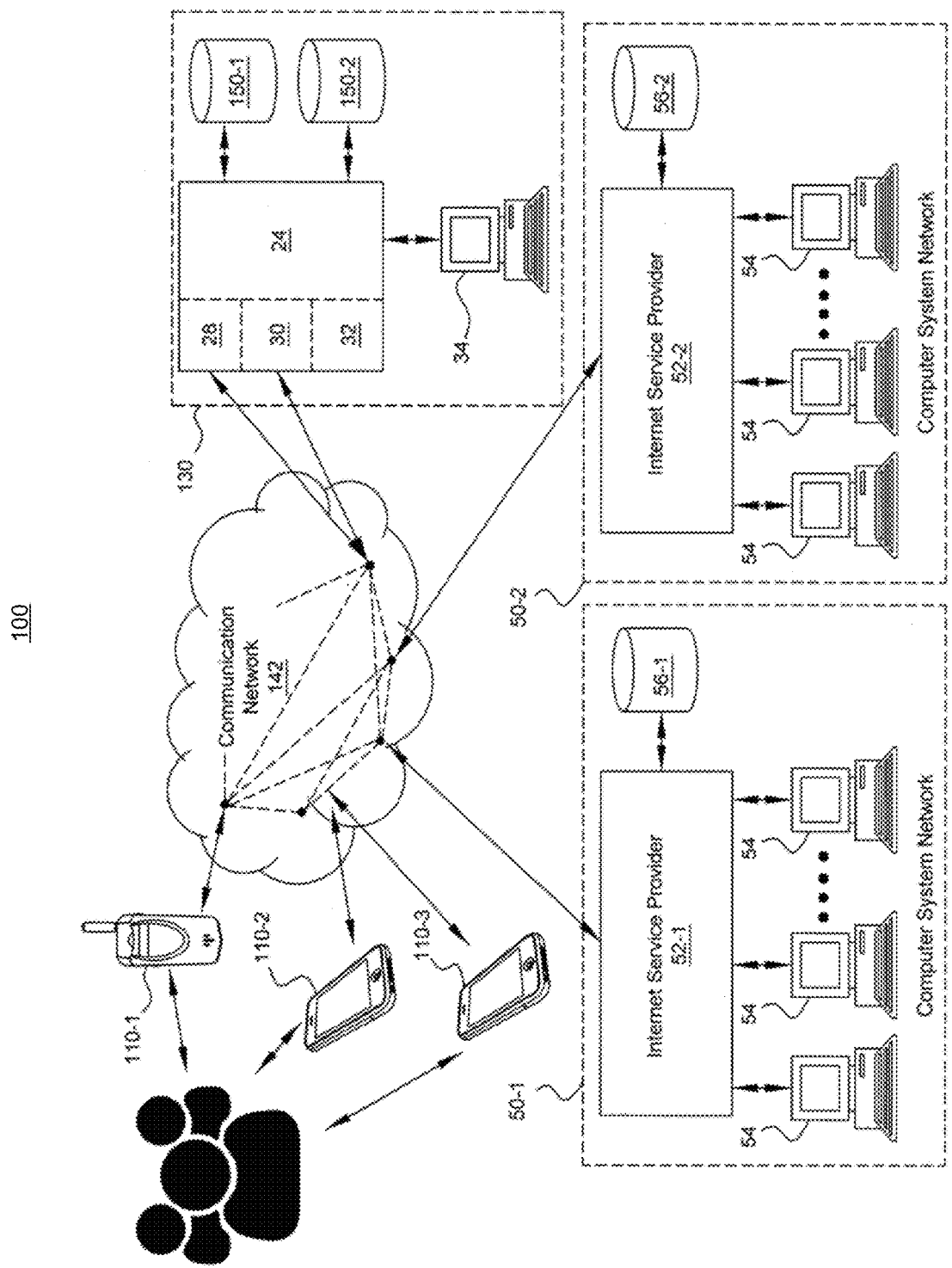
FIG. 1A illustrates one example of a system in accordance with some embodiments of the present disclosure.

In various embodiments, the PD measuring system may interact with client devices for information exchange. FIG. 1A depicts one example of a system 100 in which a plurality of client devices 110-1, 110-2, and 110-3 (collectively "client devices 110") are connected via communication network 142 to one or more computer system networks 50-1, 50-2 ("computer networks 50"), and to management server 130. Communication network 142 may be a wide area network ("WAN"), a local area network ("LAN"), personal area network ("PAN"), or the like. In one embodiment, communication network 142 is the Internet and client devices 110 are online. "Online" may mean connecting to or accessing source data or information from a location remote from other devices or networks coupled to communication network 142.

Management server 130 includes a processing unit 24 coupled to one or more data storage units 150-1, 150-2 (collectively referred to as "database management system 150" or "DBMS 150"). The processing unit 24, in some embodiments is configured to provide front-end graphical user interfaces ("GUI") (e.g., PD measurement GUI 28 and client users GUI 30), and a back-end or administrative graphical user interface or portal 32 to one or more remote computers 54 or to one or more local computers 34. In some embodiments, a PD measurement interface, described in further detail below, is provided that accesses management server 130 via GUI 28. The GUIs can take the form of, for example, a webpage that is displayed using a browser program local to remote computers 54 or to one or more local computers 34. It is understood that the system 100 may be implemented on one or more computers, servers, or other computing devices. In some embodiments, the GUI may be displayed on client devices 110 via a software application. For example, system 100 may include additional servers programmed or partitioned based on permitted access to data stored in DBMS 150. As used herein, "portal" is not limited to general-purpose Internet portals, such as YAHOO!® or GOOGLE®, but also includes GUIs that are of interest to specific, limited audiences and that provide the party access to a plurality of different kinds of related or unrelated information, links and tools as described below. "Webpage" and "website" may be used interchangeably herein.

Remote computers 54 may be part of a computer system network 50-1, 50-2 and gain access to communication network 142 through an Internet service provider ("ISP") 52-1, 52-2 ("ISPs 52"). Client devices 110 may gain access to communications network 142 through a wireless cellular communication network, a WAN hotspot, or through a wired or wireless connection with a computer as will be understood by one skilled in the art. Client users and administrative personnel, as will be described below, may use remote computers 54 and/or client devices 110 to gain access to system 100. Computer system network 50-1, 50-2, may include one or more data storage units 56-1, 56-2.

In one embodiment, client devices 110 includes any mobile device capable of transmitting and receiving wireless signals. Examples of mobile instruments include, but are not limited to, mobile or cellular phones, smart phones. personal digital assistants ("PDAs"), laptop computers, tablet computers, music players, and e-readers, to name a few possible devices.

Figure 1B:
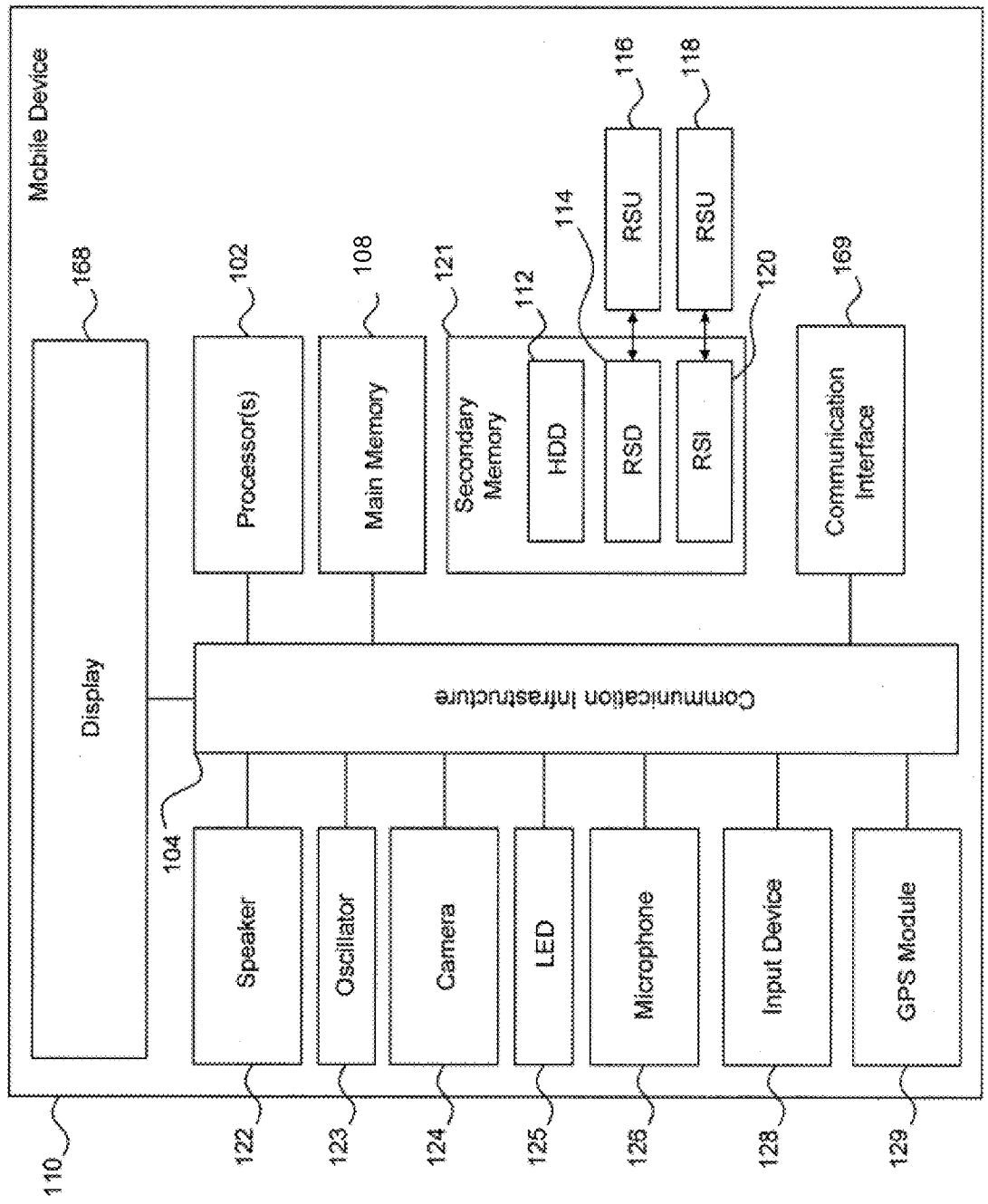
FIG. 1B illustrates one example of an architecture of a mobile device in accordance with some embodiments of the present disclosure.

FIG. 1B is a block diagram of one example of an architecture of client device 110. As shown in FIG. 1B, client device 110 includes one or more processors, such as processor(s) 102. Processor(s) 102 may be any central processing unit ("CPU"), microprocessor, micro-controller, or computational device or circuit for executing instructions. Processor(s) are connected to a communication infrastructure 104 (e.g., a communications bus, cross-over bar, or network). Various software embodiments are described in terms of this exemplary client device 110. After reading this description, it will be apparent to one of ordinary skill in the art how to implement the method using client devices 110 that include other systems or architectures. One of ordinary skill in the art will understand that computers 34, 54 may have a similar and/or identical architecture as that of client devices 110. Put another way, computers 34, 54 can include some, all, or additional functional components as those of the client device 110 illustrated in FIG. 1B.

Client device 110 includes a display 168 that displays graphics, video, text, and other data received from the communication infrastructure 104 (or from a frame buffer not shown) to a user (e.g., a subscriber, commercial user, back-end user, or other user). Examples of such displays 168 include, but are not limited to, LCD screens, OLED display, capacitive touch screen, and a plasma display, to list only a few possible displays. Client device 110 also includes a main memory 108, such as a random access ("RAM") memory, and may also include a secondary memory 110. Secondary memory 121 may include a more persistent memory such as, for example, a hard disk drive ("HDD") 112 and/or removable storage drive ("RSD") 114, representing a magnetic tape drive, an optical disk drive, solid state drive ("SSD"), or the like. In some embodiments, removable storage drive 114 reads from and/or writes to a removable storage unit ("RSU") 116 in a manner that is understood by one of ordinary skill in the art. Removable storage unit 116 represents a magnetic tape, optical disk, or the like, which may be read by and written to by removable storage drive 114. As will be understood by one of ordinary skill in the art, the removable storage unit 116 may include a tangible and non-transient machine readable storage medium having stored therein computer software and/or data.

In some embodiments, secondary memory 110 may include other devices for allowing computer programs or other instructions to be loaded into client device 110. Such devices may include, for example, a removable storage unit ("RSU") 118 and a corresponding interface ("RSP") 120. Examples of such units 118 and interfaces 120 may include a removable memory chip (such as an erasable programmable read only memory ("EPROM")), programmable read only memory ("PROM")), secure digital ("SD") card and associated socket, and other removable storage units 118 and interfaces 120, which allow software and data to be transferred from the removable storage unit 118 to client device 110.

Client device 110 may also include a speaker 122, an oscillator 123, a camera 124, a light emitting diode ("LED") 125, a microphone 126, an input device 128, an accelerometer (not shown), and a global positioning system ("GPS") module 129. Examples of camera 124 features include, but are not limited to optical image stabilization ("OIS"), larger sensors, bright lenses, 4K video, optical zoom plus RAW images and HDR, "Bokeh mode" with multi lenses and multi-shot night modes. Camera 124 may comprise one or more lenses with different functions. By way of example, camera 124 may include an ultrawide sensor, telephoto sensor, time of flight sensor, macro sensor, megapixel ("MP") sensor, and/or a depth sensor. Camera 124, as described herein, is not limited to a single camera. Camera 124 may include a camera system that includes multiple different types of cameras, sensors, etc. By way of example, Apple® released a TrueDepth® camera system that includes a 7 MP front-facing "selfie" camera, infrared emitter, infrared camera, proximity sensor, ambient light sensor, flood illuminator, and dot projector that cooperate to obtain depth map and associated image. In other words, camera 124 of client device 110 may have multiple sensors, cameras, emitters, or other associated components that work as a system to obtain image information for use by client device 110.

Examples of input device 128 include, but are not limited to, a keyboard, buttons, a trackball, or any other interface or device through which a user may input data. In some embodiment, input device 128 and display 168 are integrated into the same device. For example, display 168 and input device 128 may be touchscreen through which a user uses a finger, pen, and/or stylus to input data into client device 110.

Client device 110 also includes one or more communication interfaces 169, which allows software and data to be transferred between client device 110 and external devices such as, for example, another client device 110, a computer 34, 54 and other devices that may be locally or remotely connected to system 100. Examples of the one or more communication interfaces 169 may include, but are not limited to, a modem, a network interface (such as an Ethernet card or wireless card), a communications port, a Personal Computer Memory Card International Association ("PCMCIA") slot and card, one or more Personal Component Interconnect ("PCI") Express slot and cards, or any combination thereof. The one or more communication interfaces 169 may also include a wireless interface configured for short range communication, such as near field communication ("NFC"), Bluetooth, or other interface for communication via another wireless communication protocol. As briefly noted above, one of ordinary skill in the art will understand that computers 34, 54 and portions of system 100 may include some or all components of client device 110.

Software and data transferred via the one or more communications interfaces 169 are in the form of signals, which may be electronic, electromagnetic, optical, or other signals capable of being received by communications interfaces 169. These signals are provided to communications interface 169 via a communications path or channel. The channel may be implemented using wire or cable, fiber optics, a telephone line, a cellular link, a radio frequency ("RF") link, or other communication channels.

In this application, the terms "non-transitory computer program medium" and "non-transitory computer readable medium" refer to media such as removable storage units 116, 118, or a hard disk installed in hard disk drive 112. These computer program products provide software to client device 110. Computer programs (also referred to as "computer control logic") may be stored in main memory 108 and/or secondary memory 110. Computer programs may also be received via the one or more communications interfaces 169. Such computer programs, when executed by a processor(s) 102, enable the client device 110 to perform the features of the methods and systems discussed herein.

In various embodiments, as shown in FIGS. 1A & 1B, client device 110 may include a computing device such as a hashing computer, a personal computer, a laptop computer, a tablet computer, a notebook computer, a hand-held computer, a personal digital assistant, a portable navigation device, a mobile phone, a smart phone, a wearable computing device (e.g., a smart watch, a wearable activity monitor, wearable smart jewelry, and glasses and other optical devices that include optical head-mounted displays ("OHMDs")), an embedded computing device (e.g., in communication with a smart textile or electronic fabric), or any other suitable computing device configured to store data and software instructions, execute software instructions to perform operations, and/or display information on a display device. Client device 110 may be associated with one or more users (not shown). For example, a user operates client device 110, causing it to perform one or more operations in accordance with various embodiments.

Client device 110 includes one or more tangible, non-transitory memories that store data and/or software instructions, and one or more processors configured to execute software instructions. Client device 110 may include one or more display devices that display information to a user and one or more input devices (e.g., keypad, keyboard, touch-screen, voice activated control technologies, or any other suitable type of known input device) to allow the user to input information to the client device. Client device 110 processor(s) may be any central processing unit ("CPU"), microprocessor, micro-controller, or computational device or circuit for executing instructions. Processor(s) are connected to a communication infrastructure (e.g., a communications bus, cross-over bar, or network). Various software embodiments are described in terms of this exemplary client device 110. After reading this description, it will be apparent to one of ordinary skill in the art how to implement the method using client device 110 that include other systems or architectures. One of ordinary skill in the art will understand that computers may have a similar and/or identical architecture as that of client device 110. Put another way, computers can include some, all, or additional functional components as those of the client device 110 illustrated in FIGS. 1A & 1B.

Client device 110 also includes one or more communication interfaces 169, which allows software and data to be transferred between client device 110 and external devices such as, for example, another client device 110, and other devices that may be locally or remotely connected to client device 110. Examples of the one or more communication interfaces may include, but are not limited to, a modem, a network interface (e.g., communication interface 169, such as an Ethernet card or wireless card), a communications port, a PCMCIA slot and card, one or more PCI Express slot and cards, or any combination thereof. The one or more communication interfaces 169 may also include a wireless interface configured for short range communication, such as NFC, Bluetooth, or other interface for communication via another wireless communication protocol.

Software and data transferred via the one or more communications interfaces 169 are in the form of signals, which may be electronic, electromagnetic, optical, or other signals capable of being received by communications interfaces. These signals are provided to communications interface 169 via a communications path or channel. The channel may be implemented using wire or cable, fiber optics, a telephone line, a cellular link, a radio frequency ("RF") link, or other communication channels.

In an embodiment where the system 100 or method is partially or entirely implemented using software, the software may be stored in a computer program product and loaded into client device 110 using removable storage drive, hard drive, and/or communications interface. The software, when executed by processor(s), causes the processor(s) to perform the functions of the method described herein. In another embodiment, the method is implemented primarily in hardware using, for example, hardware components such as application specific integrated circuits ("ASICs"). Implementation of the hardware state machine so as to perform the functions described herein will be understood by persons skilled in the art. In yet another embodiment, the method is implemented using a combination of both hardware and software.

Embodiments of the subject matter described in this specification can be implemented in a system 100 that includes a back end component, e.g., as a data server, or that includes a middleware component, e.g., an application server, or that includes a front end component (e.g., a client device 110) having a graphical user interface or a Web browser through which a user can interact with an implementation of the subject matter described is this specification, or any combination of one or more such back end, middleware, or front end components. The components of the system can be interconnected by any form or medium of digital data communication, (e.g., a communication network 142). Communications network 142 may include one or more communication networks or media of digital data communication. Examples of communication network 142 include a local area network ("LAN"), a wireless LAN, a RF network, a NFC network, (e.g., a "WiFi" network), a wireless Metropolitan Area Network ("MAN") connecting multiple wireless LANs, NFC communication link(s), and a wide area network ("WAN"), e.g., the Internet and combinations thereof. In accordance with various embodiments of the present disclosure, communications network 142 may include the Internet and any publicly accessible network or networks interconnected via one or more communication protocols, including, but not limited to, hypertext transfer protocol ("HTTP") and HyperText Transfer Protocol Secured ("HTTPS") and Secured Socket Layer/Transport Layer Security ("SSL/TLS") and transmission control protocol/internet protocol ("TCP/IP"). Communications protocols in accordance with various embodiments also include protocols facilitating data transfer using radio frequency identification ("RFID") communications and/or NFC. Moreover, communications network 142 may also include one or more mobile device networks, such as a GSM or LTE network or a PCS network, allowing a client device to send and receive data via applicable communications protocols, including those described herein. For ease of illustration, communication network 142 is shown as an extension of management server 130.

A client device 110 and server 130 are generally remote from each other and typically interact through a communication network 142. The relationship of client device 110 and management server 130 arises by virtue of computer programs running on the respective system components and having a client-server relationship to each other. System 100 may include a web/application server (not shown) in embodiments used to gain access to many services provided by management server 130.

In one aspect, client device 110 stores in memory one or more software applications that run on the client device and are executed by the one or more processors. In some instances, each client device stores software applications that, when executed by one or more processors, perform operations that establish communications with management server 130 (e.g., across communication network 142 via communication interface 169) and that obtain, from management server 130, information or data via database management system 150 in accordance with various embodiments.

In various embodiments, client device 110 may execute stored software application(s) to interact with management server 130 via a network connection. The executed software applications may cause client device 110 to communicate information (e.g., facial measurements (e.g., PD), user profile information, etc.). As described below, executed software applications (s) may be configured to allow a user associated with client device 110 to obtain a PD measurement using camera 124. Stored software application(s) on client device 110 are configured to access webpages on the Internet or other suitable network based communication capable of interacting with communication network 142, as would be understood by one of ordinary skill in the art. For example, a user may access a user account on management server 130 via an Internet webpage. In this example, management server 130 is configured to render the Internet webpage for the user on client device 110. Alternatively, management server 130 may provide information to stored software application(s) on client device 110 via communication network 142. In this example, client device 110 will display information provided by management server 130 using a stored software application(s) graphical user interface display. In the example above, a respective user account may be associated with a developer, client user, or supervisor/monitoring authority as would be understood by one of ordinary skill in the art and described below.

According to various embodiments, system 100 includes database management system/storage 150 for managing and storing data, for example, facial measurement information (e.g., PD, etc.), user account authentication information, and other data maintained by the management server 130. The database management system and/or storage are referred to herein simply as DBMS 150 for convenience. DBMS 150 may be communicatively coupled with various modules and engines (not illustrated).

It should be understood that various forms of data storage or repositories can be used in system 100 that may be accessed by a computing system, such as hard drives, tape drives, flash memory, random-access memory, read-only memory, EEPROM storage, in-memory databases like SAP HANA, and so on, as well as any combination thereof. Stored data may be formatted within data stores in one or more formats, such as flat text file storage, relational databases, non-relational databases, XML, comma-separated values, Microsoft Excel files, or any other format known to those of ordinary skill in the art, as well as any combination thereof as is appropriate for the particular use. Data stores may provide various forms of access to the stored data, such as by file system access, network access, a SQL protocol (e.g., ODBC), HTTP, FTP, NES, CIFS, and so on, as well as any combination thereof.

According to various embodiments, client device 110 is configured to access DBMS 150 via management server 130. In various embodiments, DBMS 150 is configured to maintain a database schema. For example, a database schema may be arranged to maintain identifiers in columns within DBMS 150 associated with facial measurement or user account information. In this aspect, identifiers refer to specific information pertaining to the categories described above. A database schema within DBMS 150 may be arranged or organized in any suitable manner within the system. Although the above-described examples identify categorical identifiers, any number of suitable identifiers may be used to maintain records associated with the system described herein. In addition, a database schema may contain additional categories and identifiers not described above for maintaining record data in system 100. The database can also provide statistics and marketing information associated with users of system 100.

The database schema described above advantageously organizes identifiers in a way that permits the system to operate more efficiently. In some embodiments, categories of identifiers in the database schema increase efficiency by grouping identifiers with an associated management model of management server 130.

In various embodiments, management server 130 includes computing components configured to store, maintain, and generate data and software instructions. For example, management server 130 may include or have access to one or more processors 24, one or more servers (not shown) and tangible, non-transitory memory devices (e.g., local data store (in addition to DBMS 150)) for storing software or code for execution and/or additional data stores. Servers may include one or more computing devices configured to execute software instructions stored on to perform one or more processes in accordance with various embodiments. In some embodiments, DBMS 150 includes a server that executes software instructions to perform operations that provide information to at least one other component of computing environment 100, for example providing data to another data store or to third party recipients (e.g., banking systems, third party vendors, information gathering institutions, etc.) through a network, such as a communication network 142.

Management server 130 may be configured to provide one or more websites, digital portals, or any other suitable service that is configured to perform various functions of management server 130 components. In some embodiments, management server 130 maintains application programming interfaces ("APIs") through which the functionality and services provided by server 130 may be accessed through one or more application programs executed by a client device 110. In various embodiments, management server 130 may provide information to software application(s) on client device 110 for display on a graphical user interface 168.

In some embodiments, management server 130 provides information to client device 110 (e.g., through the API associated with the executed application program). Client device 110 presents portions of the information to corresponding users through a corresponding respective graphical user interface 168 or webpage.

In various embodiments, management server 130 is configured to provide or receive information associated with services provided by management server 130 to client device 110. For example, client device 110 may receive information via communication network 142, and store portions of the information in a locally accessible store device and/or network-accessible storage devices and data stores (e.g., cloud-based storage). For example, client device 110 executes stored instructions (e.g., an application program, a web browser, and/or a mobile application) to process portions of stored data and render portions of the stored data for presentation to the respective user or users Management server 130 may include additional servers (not shown) which may be incorporated as a corresponding node in a distributed network or as a corresponding networked server in a cloud-computing environment. Furthermore, servers may communicate via communication network 142 with one or more additional servers (not shown), that may facilitate the distribution of processes for parallel execution by the additional servers.

PD Process Management

Figure 2:
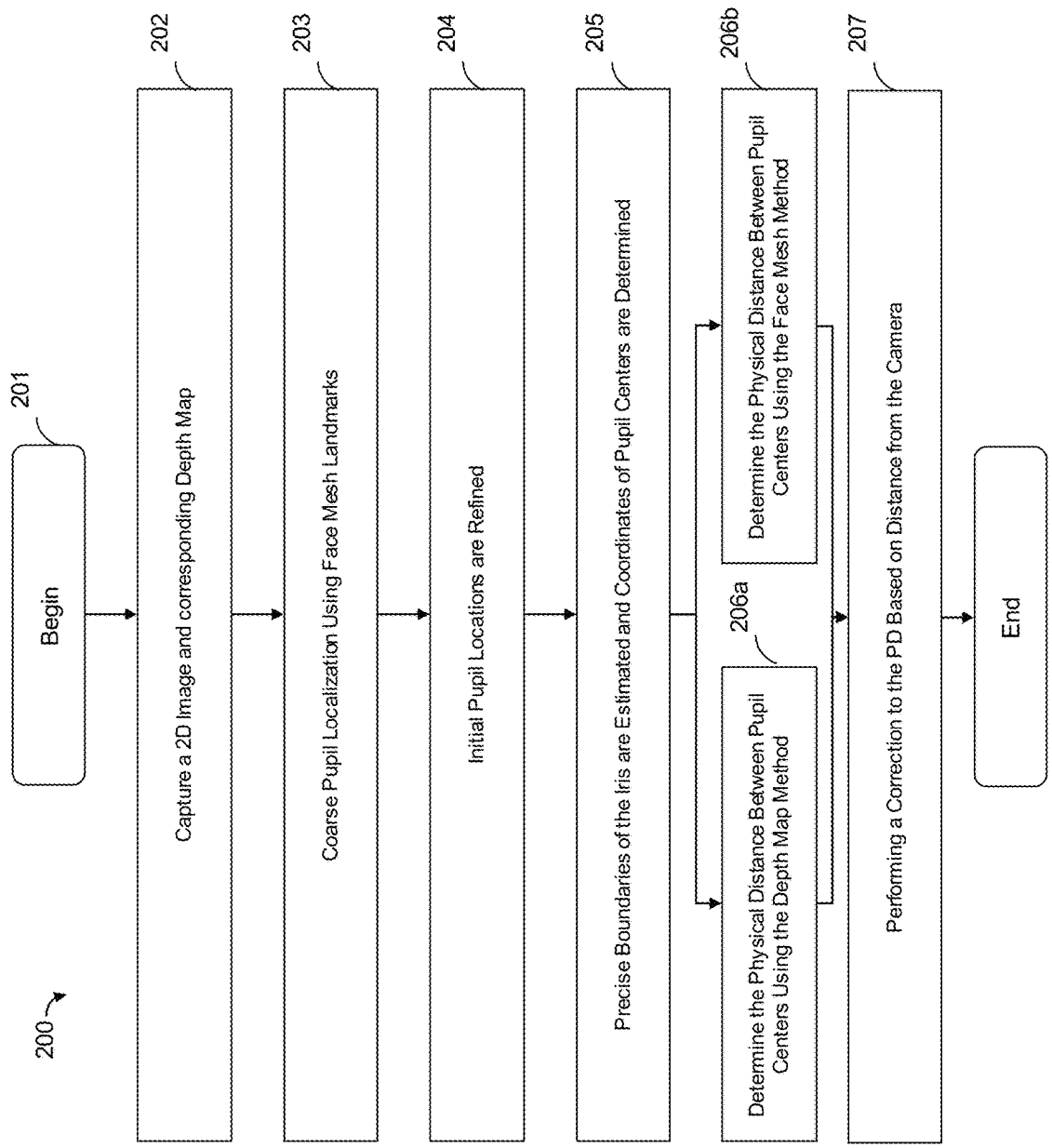
FIG. 2 is a flow diagram illustrating an example PD measurement process using a depth map in accordance with some embodiments of the present disclosure.
Figure 9:
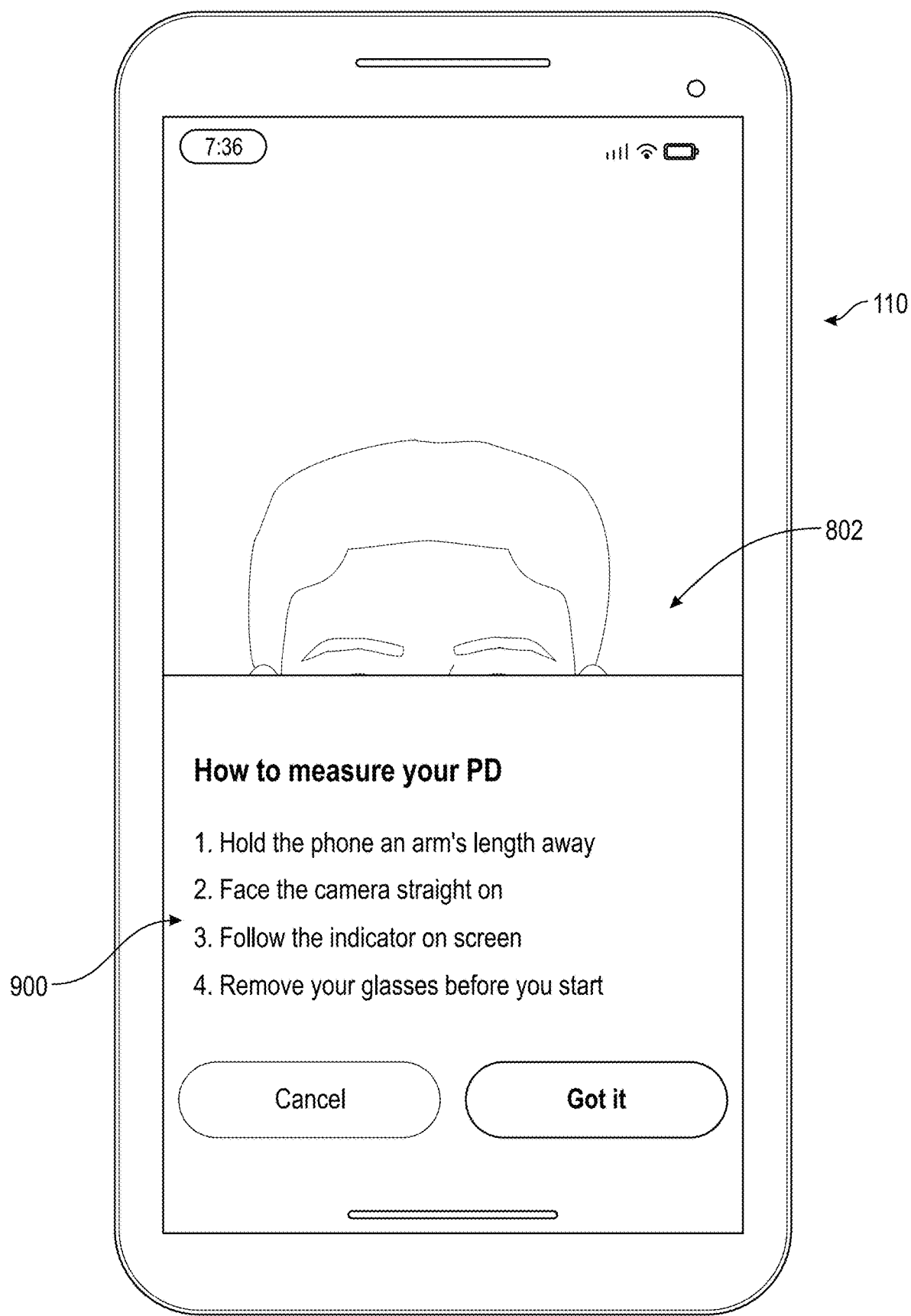
Figure 10:
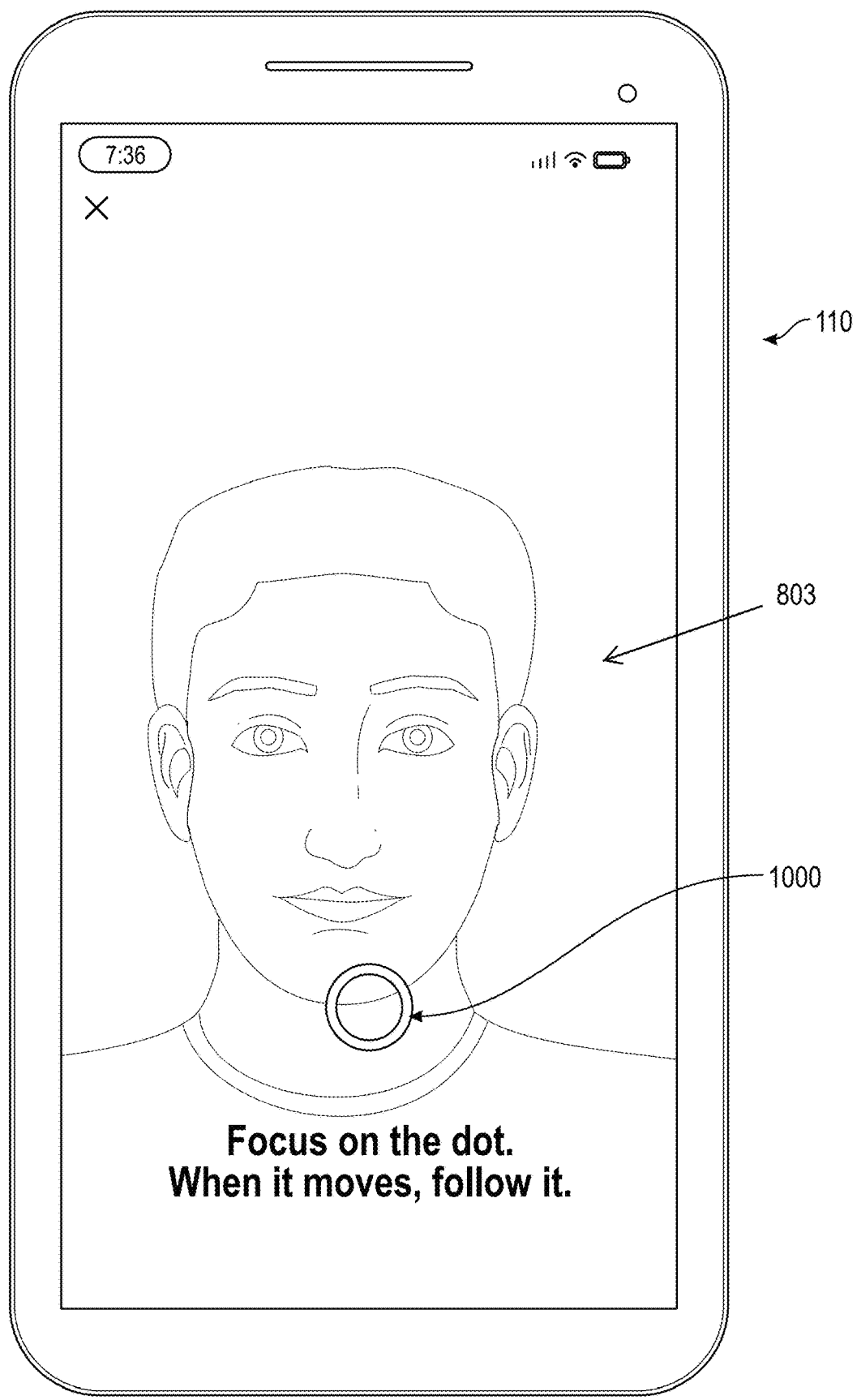
Figure 11:
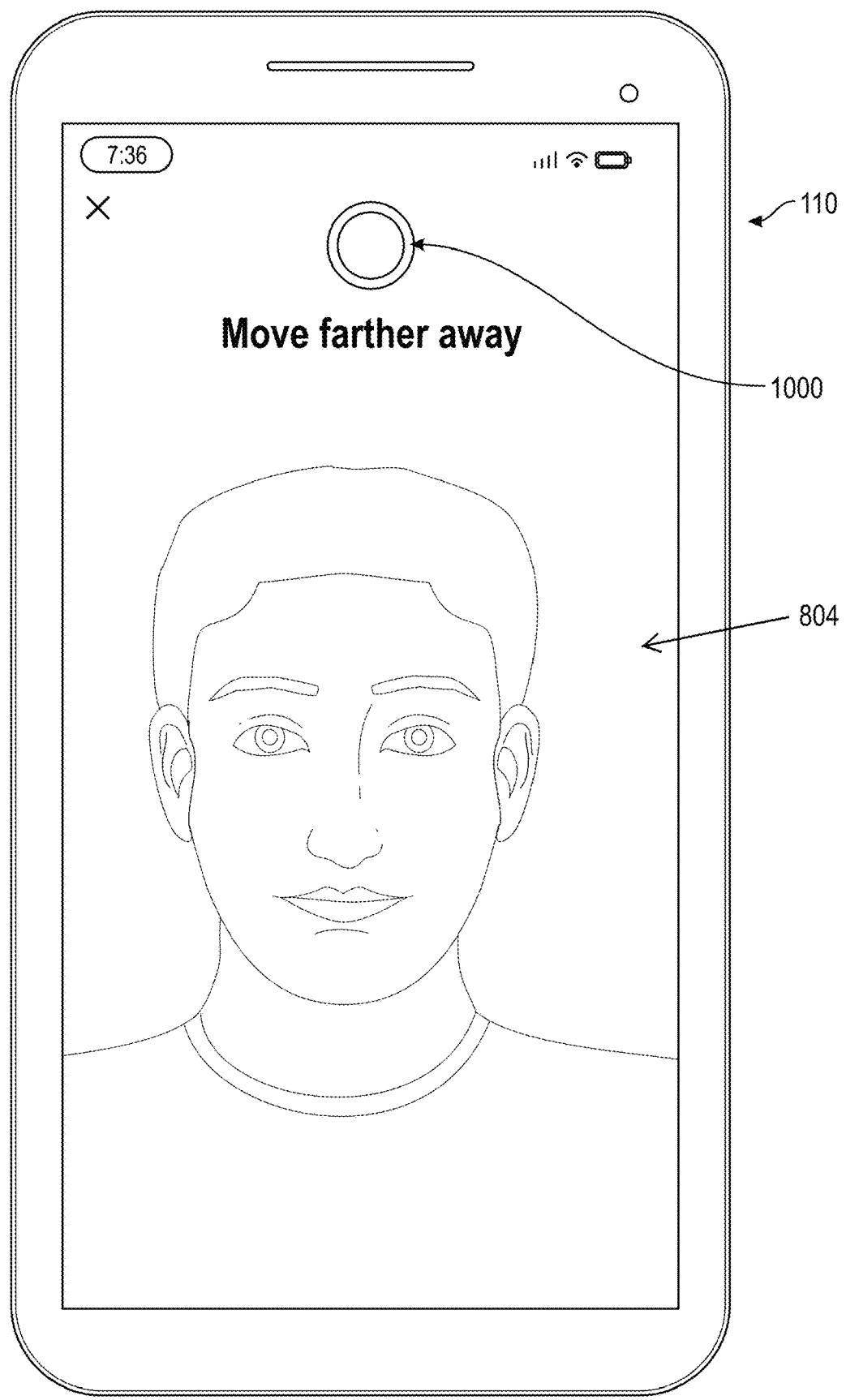

In various embodiments of the present disclosure, a process for measuring or estimating the PD of a user on client device 110 is provided. Referring now to FIG. 2, a flow diagram illustrating an example PD measurement process 200 using a depth map in accordance with some embodiments of the present disclosure. Initially, at step 202, an image is captured by a user on client device 110 via at least one camera (such as camera 124). In some embodiments, instructions to use the PD system (as shown, for example, instructions 900 in FIG. 9) are provided to the user prior to using the PD system. In some embodiments, feedback is provided to the user regarding whether his/her head is appropriately positioned for an accurate measurement (i.e., whether the head is in a position for an accurate image capture). Such feedback, which is conveyed through, for example, text, verbal and/or symbol format, directs the user to move his/her head and/or client device 110 in various directions, such as farther away, closer, up, down, right, left, diagonally, rotate clockwise or rotate counterclockwise, and/or to look at a spot or area on the screen of client device 110 or offscreen. The feedback can include one or more indicators on the screen of client device 110 that the user can follow with his/her head and/or eyes. As the user follows the feedback, the user eventually positions his/her head for an accurate measure. By way of example, FIGS. 10 and 11 show exemplary indicator 1000 with text directions instructing the user to "Focus on this dot. When it moves, follow it." As the indicator moves from a starting position to an end position on the screen of client device 110, the user will move his/her head and/or eyes in accord with the indicator. Additional feedback, such as, for example, "Move farther away" as shown in FIG. 10, can be conveyed to the user to further move his/her head and/or eyes and/or client device 110 with at least one camera (such as camera 124) prior to image capture. Once the user's head is appropriately positioned for an accurate measure, an image is captured by the user on client device 110 via at least one camera (such as camera 124). The feedback described above may occur in connection with step 202. According to various embodiments, the image that is captured is a 2D image and corresponding depth map. In some embodiments, this depth map is obtained using a TrueDepth® camera. By way of example, a TrueDepth® camera emits an array of infrared dots (e.g., 30,000 dots) in a known pattern on the subject and an infrared sensor records how the dots interact with the scene, and a 3D structure is generated from that information. The TrueDepth® camera includes a proximity sensor for activation and an ambient light sensor for setting the output light levels. The 3D information may be used to determine the physical size of a photographed object. Although the TrueDepth® camera is disclosed in connection with this embodiment, a person of ordinary skill in the art would understand that various other depth sensing cameras may be used to perform the processes in the system and method described herein (e.g., The Point Cloud Depth Camera™, Intel RealSense®, Kinect® depth camera, Depth+Multi-Spectral Camera™ etc.).

In various embodiments, the 2D image and corresponding 3D depth map may be obtained from a storage unit on client device 110. In some embodiments, the 2D image and corresponding 3D depth map information may be received by a client device 110 to conduct the processes described herein. It should be appreciated, that a 2D image and corresponding 3D depth map may be obtained by a different device and/or be generated in a non-contemporaneous manner from the steps described herein.

Figure 3:
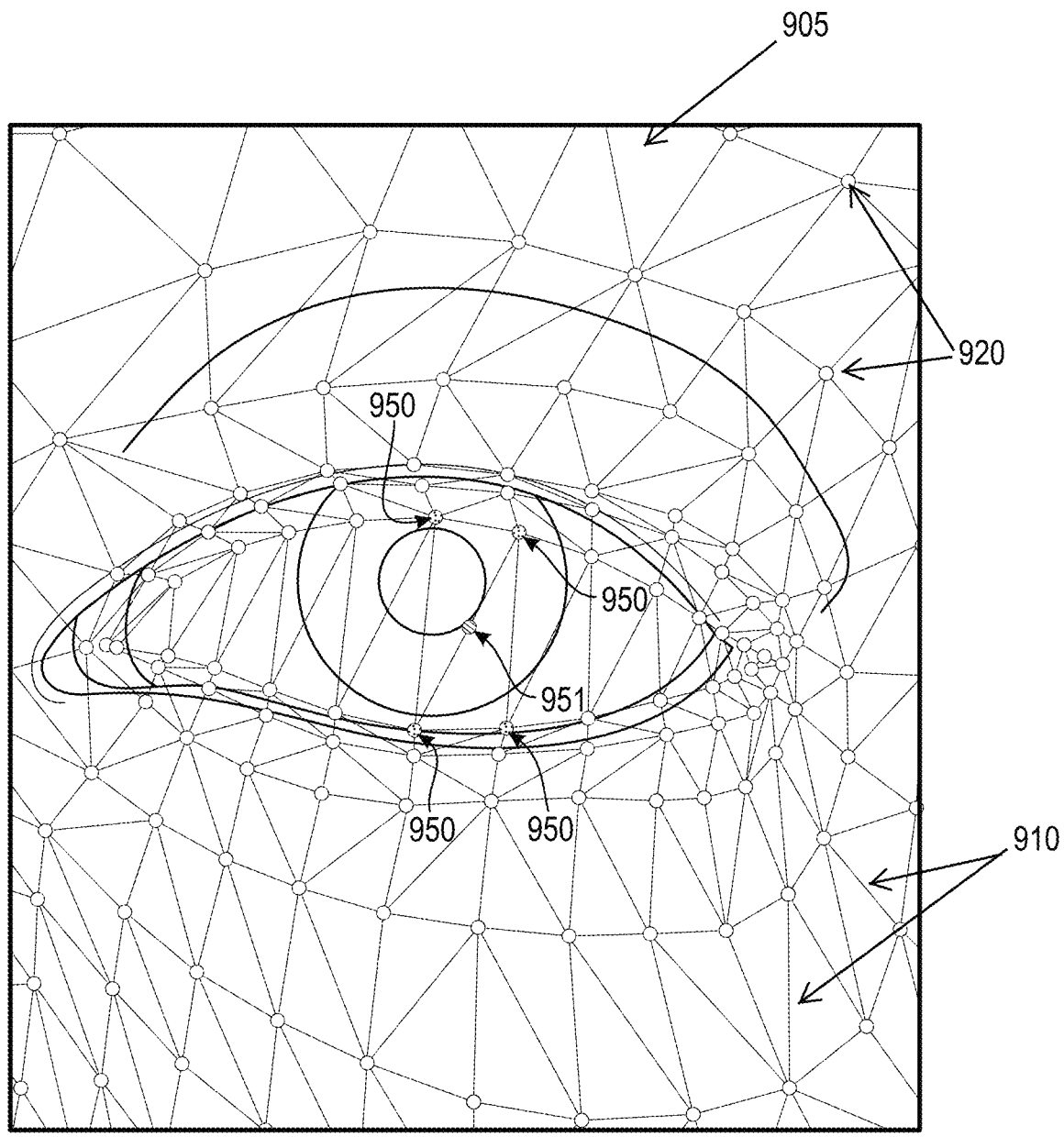
FIG. 3 is an example image of a user's pupil region with a face mesh 905 (depicted by a plurality of lines 910 connected to a plurality of vertices 920) superimposed in accordance with some embodiments of the present disclosure, the face mesh showing key vertices 950 and the centroid 951 of the key vertices.

In various embodiments, at step 203, coarse pupil localization is obtained using a plurality of face mesh landmarks. According to various embodiments, the 3D information identified at Step 202 is used to generate coordinates of the face mesh vertices near (e.g., 0-5 mm from the pupil) the center of the eye opening to obtain approximate locations of the pupils. By way of example, vertices 1095, 1094, 1107, and 1108 are near the right pupil, and vertices 1076, 1075, 1062, and 1063 are near the left pupil. A person of ordinary skill in the art would understand that the vertices identified in the above example may be different from the actual vertices determined and would vary based on the coordinates generated for an individual. FIG. 3 is an example image of a user's pupil region with a face mesh 905 (depicted by a plurality of lines 910 connected to a plurality of vertices 920) superimposed in accordance with some embodiments of the present disclosure, the face mesh showing key vertices 950 and the centroid 951 of the key vertices. In some embodiments, for each pupil, a 3D centroid of the vertices corresponding to each pupil are computed to determine the corresponding 2D images coordinates of the centroid. In various embodiments, this computation is performed by SceneKit's® projectPoint(_:) method or other methods that projects one or more points from a 3D world coordinate system of a scene to a 2D pixel coordinate system of a renderer. A person of ordinary skill in the art would appreciate that the computation to determine corresponding 2D image coordinates of the 3D centroid may be performed by any suitable application or system.

At step 204, according to various embodiments, the initial pupil locations obtained at step 203 are refined using a convolution with a 2D center-surround filter. In this context, convolution can be thought of as a method for finding the regions in an image that best match the appearance of a test pattern known as a kernel. In some embodiments, a kernel with a dark circle surrounded by a white annulus is used to find regions in the image that resemble the kernel. In various embodiments, the convolution method may be run multiple times with kernels of varying sizes if the pattern to be localized has an unknown size. In some embodiments, a pupil size estimate (e.g., approximately 12 mm in diameter; approximately =+/−2 mm) may be used to determine the approximate distance of the eye from the camera using the associated face mesh. Using the pupil size estimate and the following formula, a prediction can be made for how large the iris will appear in the image:

The iris's pixel diameter D is given by:

$$D = \left(\frac{f}{z}\right)d$$

wherein $f$ is the focal length of 2D camera, z is the distance between the camera and the pupil and d is the iris diameter, which is assumed to be approximately 12 mm.

According to various embodiments, the kernel is structured as follows: It has a center circular region of diameter D with a magnitude of −(⅘) and a surround circular region of diameter 1.5D with a magnitude of (⅘). In this example, the magnitudes are chosen so that the kernel will produce a response of zero on a uniform image. The convolution is applied in a 3D×3D region around the initial estimate, and the location within the region that gives the strongest response is taken to be the refined estimate.

Figure 4:
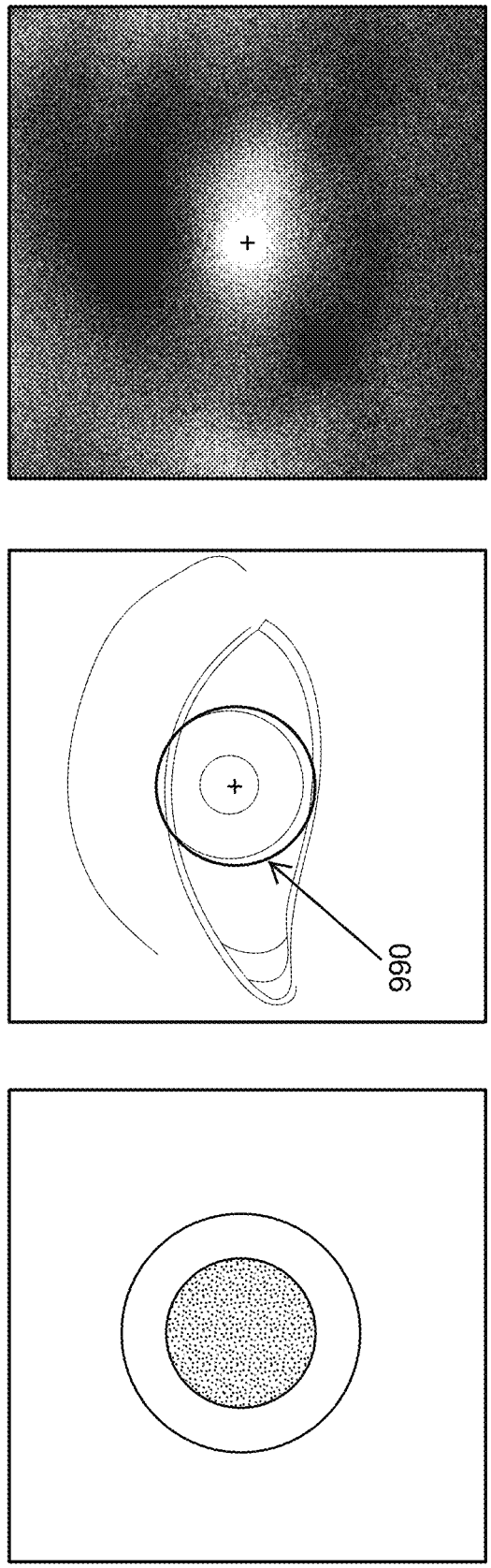
FIGS. 4A-4C show an example illustrative representation of refining initial pupil locations using convolution with a 2D image in accordance with some embodiments of the present disclosure.

FIGS. 4(a)-4(c) are an example illustrative representation of refining initial pupil locations using convolution with a 2D image of step 204 in accordance with some embodiments of the present disclosure, wherein FIG. 4A shows a filter kernel (or kernel) with center-surround structure; FIG. 4B shows an image patch with a circle 990 with a cross symbol illustrating the location with the maximum response to the kernel; and FIG. 4C shows an image response to convolution with the kernel.

At step 205, in a final pupil location refinement step, precise boundaries of the iris are estimated and robust fit of the boundaries is performed with a circle. According to various embodiments, a 1.5D pixels-wide region centered around the result from the previous localization step at 204 is considered. For each region, a horizontal gradient kernel is applied to the left and right halves of the row. To the left half of the row, a [+1, 0,−1] kernel is applied, which elicits a strong response to a light-to-dark transition. To the right half of the row, a [−1, 0,+1] kernel is applied, which elicits a strong response to a dark-to-light transition. For each half row, the column with the strongest response is considered to be a candidate boundary point. To account for the fact that the entire iris is not visible and that often the top of iris is occluded more than the bottom, only rows that correspond to less than 30° up from the center of the region and 45° down from the center of the region are considered.

Figure 5:
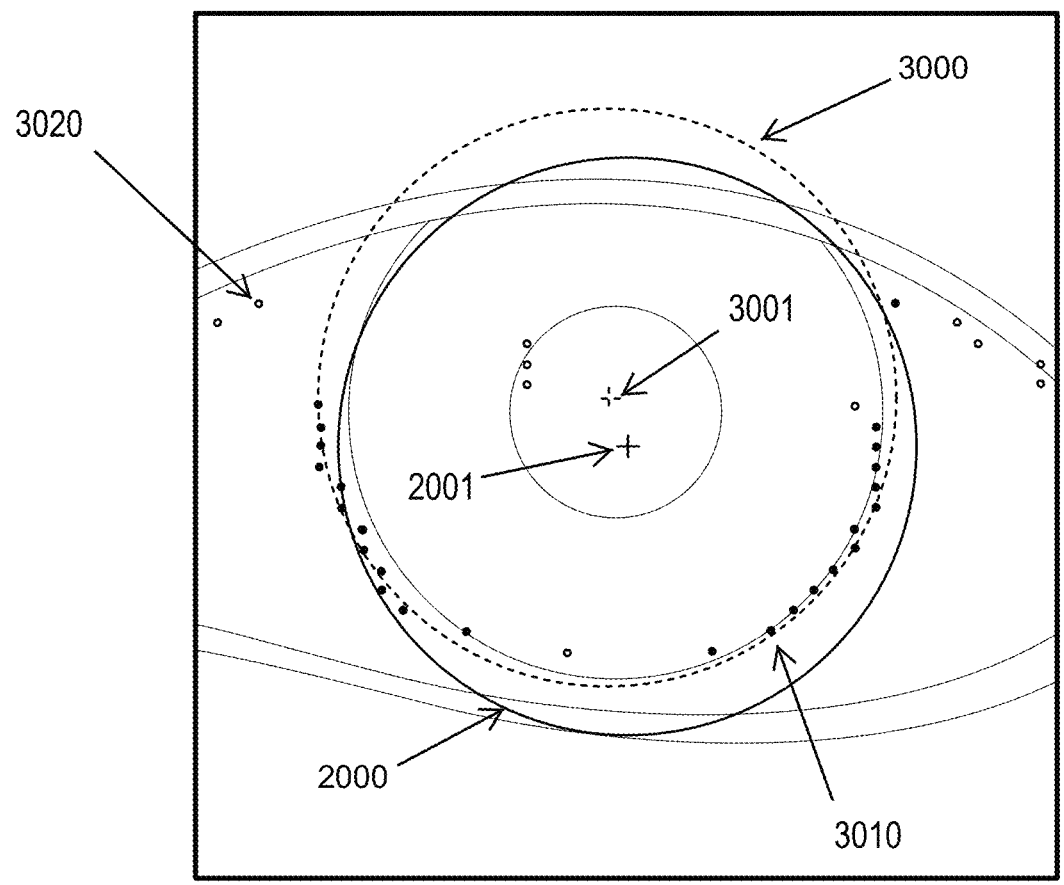
FIG. 5 is an example illustration of a random sample consensus ("RANSAC") iterative method on a pupil region image in accordance with some embodiments of the present disclosure.

FIG. 5 is an example illustration of a RANSAC iterative method on a pupil region image in accordance with some embodiments of the present disclosure. In FIG. 5, the solid-lined circle 2000 indicates the initial estimate of the iris boundary; the solid cross symbol 2001 indicates the initial estimate for the iris center; the closed dots 3010 indicate inlier boundary points; the open dots 3020 indicate outlier boundary points; the dotted-lined circle 3000 indicates the final estimate for iris boundary; and the dotted cross symbol 3001 indicates the final estimate for iris center. According to various embodiments and continuing with step 205, once candidate boundary points are identified, a circle that best fits the points needs to be determined. Because there are frequently spurious boundary points due to corneal reflections or other irregularities, it is necessary to find a way to use only the true edge points while rejecting false positives. In various embodiments, this is accomplished using a RANSAC technique. According to some embodiments, RANSAC works by fitting models to randomly selected subsets of points and choosing the one that gives the lowest error. The points that are not fit well by the final circle model are considered to be outliers and the remainder of the points are considered to be "inliers."

At step 206 (collectively 206a and 206b), the coordinates of the pupil centers are associated with a 3D coordinate system to compute the physical distance between pupil centers. In various embodiments, the physical distance between pupil centers may be computed according to the depth map method at step 206a. In this embodiment, camera calibration is used for the image frame provided by the software to obtain the z coordinates. In various embodiments, the software may be the Apple iOS™ or similar operating software for client device 110. In this embodiment, the values may be determined in the depth map that correspond to the refined location of the pupils in the 2D image.

Alternatively, according to various embodiments at step 206b, a procedure may be used to determine points on the 3D face mesh that correspond to the pupil centers. In this embodiment, a ray is fired corresponding to an image coordinate and returns the 3D world coordinates of the point at which the ray intersects with the face mesh.

Referring to step 206 (collectively 206a and 206b), according to various embodiments, using transformations provided by Apple iOS™, these 3D pupil points can be expressed in a face-centered coordinate system in which x=0 corresponds to the face midline and the x-axis corresponds to the head's transverse axis. Then the binocular PD is the x distance between the pupil locations and the monocular PDs are the x distance between the pupil locations and zero.

Figure 6:
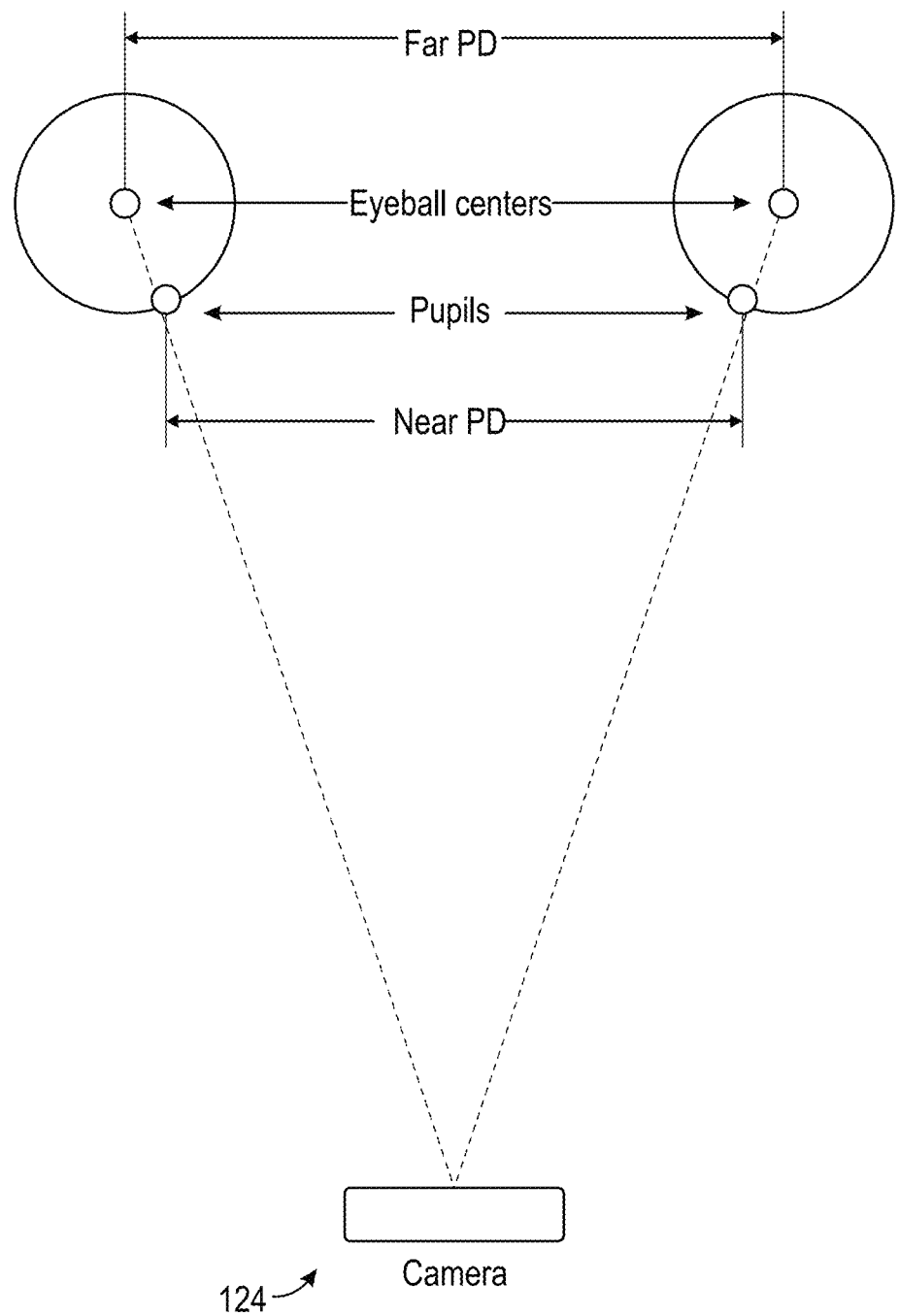
FIG. 6 is an example illustration of the process for measuring or estimating far PD in accordance with some embodiments of the present disclosure.

FIG. 6 is an example illustration of the process for measuring or estimating far PD in accordance with some embodiments of the present disclosure. At step 207, a correction to the PD is performed based on the distance that the image is taken from camera 124. For example, a client device 110 (such as a mobile device) with camera 124 is held at arm's length, which corresponds to about 400 mm. If the individual is fixating on the screen/display 168 of client device 110, their PD will be lower than their PD when they are fixating in the far distance, which is the value that is most pertinent to an accurate PD determination. Often, near PD is converted to far PD by adding a fixed value. However, in this example the fixation point distance from the subject is known, and a more principled correction can be performed. In some embodiments, it can be assumed that the eyeball transverse radius is, for example, 12 mm. Then the eyeball center coordinates can be computed by extending the ray defined by the camera coordinates and the pupil center coordinates another 12 mm. In some embodiments, the eyeball transverse radius is a range of 10 mm to 14 mm, or any intermediate value within the range. In some embodiments, the eyeball transverse radius is 10 mm; 11 mm; 12 mm; 13 mm; or 14 mm. In some embodiments, the eyeball transverse radius is approximately 12 mm (wherein "approximately" is +/−2 mm). This process is illustrated in FIG. 6.

In various embodiments, it may be desirable to aggregate multiple measurements in order to discard potential outliers. Taking the median binocular PD measurement is a straightforward way to do this. For monocular measurements, taking the median of the Oculus sinister (left eye) ("OS") and Oculus dexter (right eye) ("OD") values will likely prevent them from adding up to the median binocular value. It is more appropriate to determine the proportion of the binocular PD allocated to the OS and OD PD values, computing the median proportion, and then multiplying it by the median binocular PD value. According to various embodiments, the PD measurement is within 0.5 mm of a pupillometer measurement. In some embodiments, the PD measurement is within 1.0 mm of a pupillometer measurement.

Figure 7:
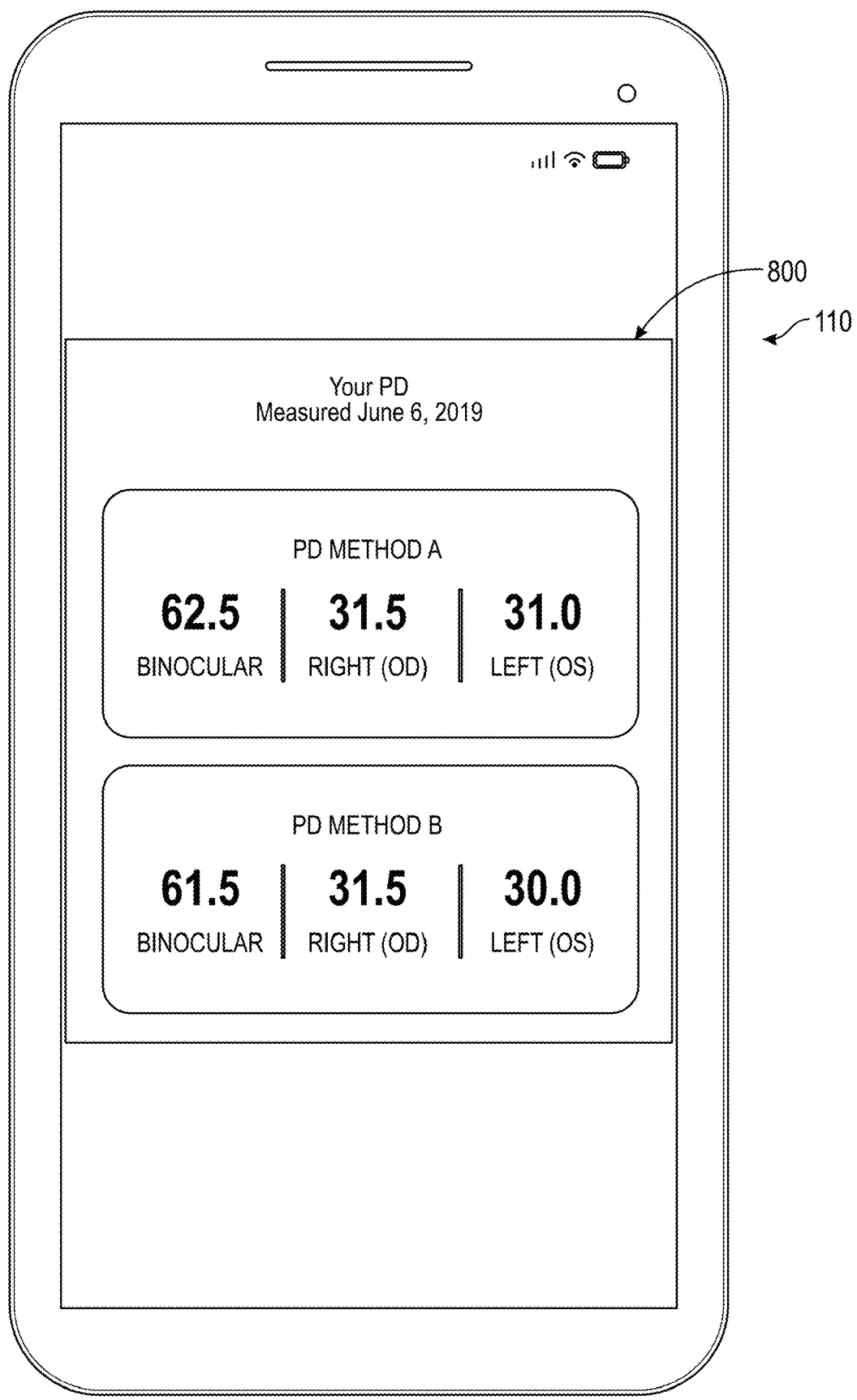
FIG. 7 is an example of a PD calculation interface 800 in accordance with some embodiments of the present disclosure. "Method A" refers to the depth map method, which is described further below. "Method B" refers to the face mesh method, which is also described further below.
Figure 8:
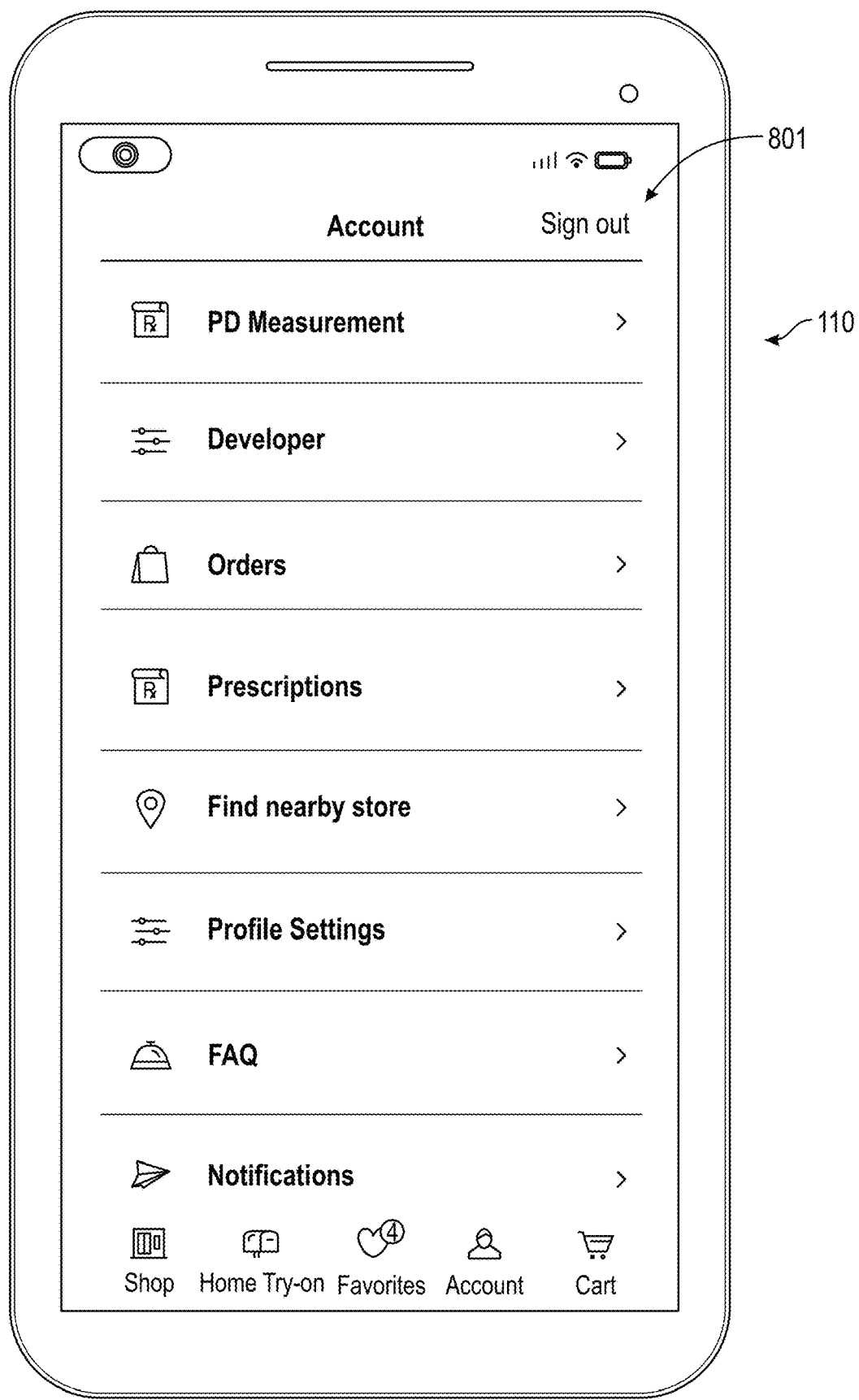
FIGS. 8-11 are example interfaces 801, 802, 803 & 804, respectively, for measuring PD in accordance with some embodiments of the present disclosure.

FIG. 7 is an example of a PD calculation interface 800 in accordance with some embodiments of the present disclosure. "Method A" refers to the depth map method, which is described herein. "Method B" refers to the face mesh method, which is also described in herein.

Figure 12:
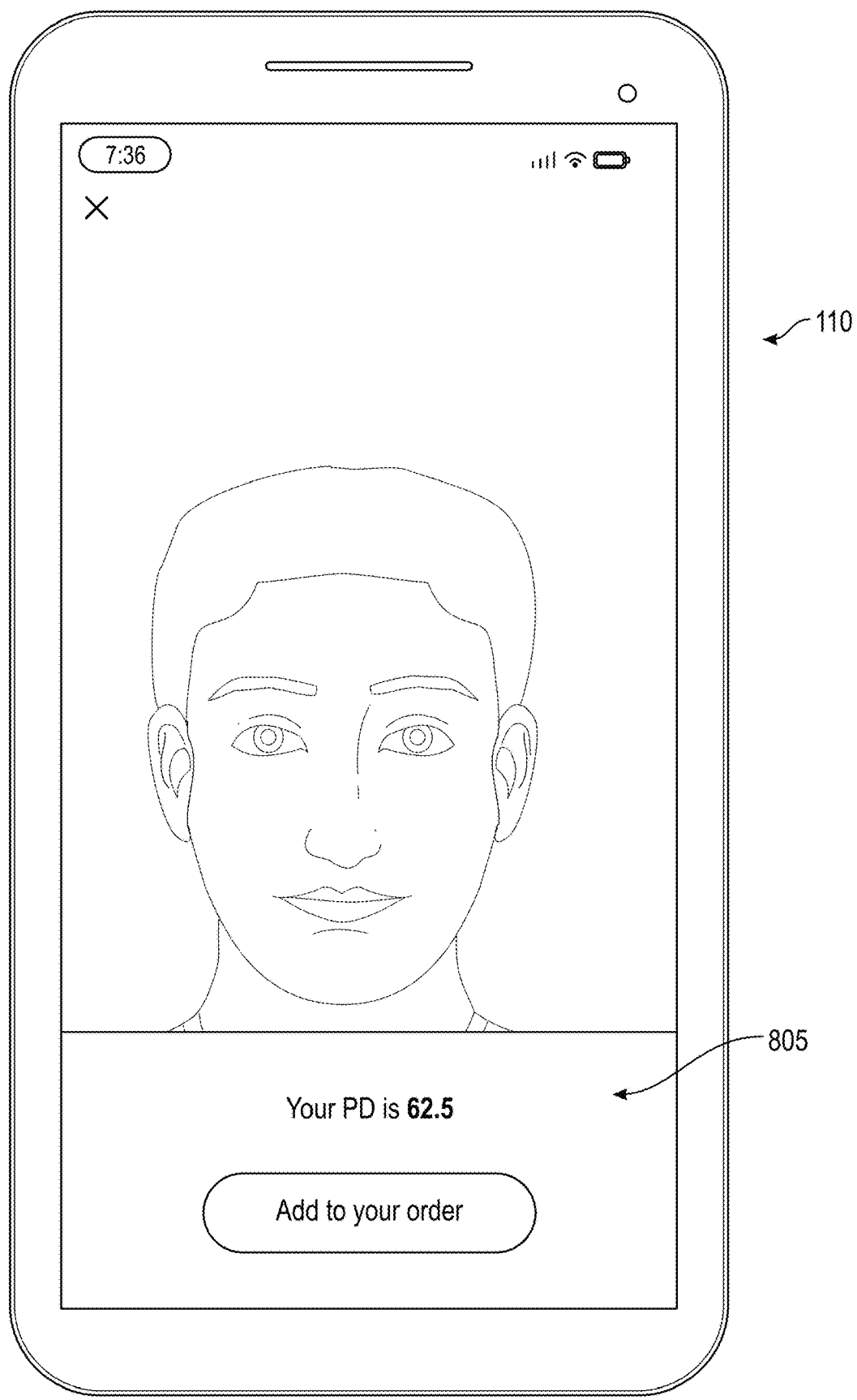
FIG. 12 is another example of a PD calculation interface 805 in accordance with some embodiments of the present disclosure.

FIGS. 8-11 are example interfaces 801, 802, 803 & 804, respectively, for measuring PD in accordance with some embodiments of the present disclosure, and FIG. 12 shows another example of a PD calculation interface 805 in accordance with some embodiments of the present disclosure. Such interfaces can be seen on the screen/display 168 of client device 110, and can also include one or more hyperlinks, weblinks, image links and/or service buttons (e.g., "Add to your order" button 1010 or other purchase-related button) to direct the user to review, select and/or purchase a product, such as eyeglasses, that requires PD info.

In various embodiments of the present disclosure system 100 may be configured to store facial measurement data (e.g., PD, etc.) for a particular user of client device 110. In various embodiments, the facial measurement data for a respective user may be associated with a user account. In some embodiments, the client device 110 may transmit facial measurement data to management server 130 for storage in DBMS 150 associated with a user account. In various embodiments, facial measurement data may be aggregated with consumer satisfaction scores or ratings to improve facial measurements processes. In some embodiments, product recommendations are provided to users of client device 110 based on facial measurement data associated with customer satisfaction scores, purchase history or other identifying characteristic such as size, thickness, and/or dimensions of a particular product.

The present disclosure can be embodied in the form of methods and apparatus for practicing those methods. The present disclosure can also be embodied in the form of program code embodied in tangible media, such as secure digital ("SD") cards, USB flash drives, diskettes, CD-ROMs, DVD-ROMs, Blu-ray disks, hard drives, or any other non-transitory machine-readable storage medium, wherein, when the program code is loaded into and executed by a machine, such as a computer, the machine becomes an apparatus for practicing the disclosure. The present disclosure can also be embodied in the form of program code, for example, whether stored in a storage medium, loaded into and/or executed by a machine, or transmitted over some transmission medium, such as over electrical wiring or cabling, through fiber optics, or via electromagnetic radiation, wherein, when the program code is loaded into and executed by a machine, such as a computer, the machine becomes an apparatus for practicing the disclosure. When implemented on a general-purpose processor, the program code segments combine with the processor to provide a unique device that operates analogously to specific logic circuits.

It may be emphasized that the above-described embodiments are merely possible examples of implementations, and merely set forth a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claims.

While this specification contains many specifics, these should not be construed as limitations on the scope of any disclosure or of what may be claimed, but rather as descriptions of features that may be specific to particular embodiments of particular disclosures. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

While various embodiments have been described, it is to be understood that the embodiments described are illustrative only and that the scope of the subject matter is to be accorded a full range of equivalents, many variations and modifications naturally occurring to those of skill in the art from a perusal hereof

What is claimed is:

1. A method of operating a pupillary distance ("PD") system, the method comprising the steps of:
    capturing, with at least one camera of the pupillary distance system, a first 2D image and a corresponding 3D depth map of a face of a subject;
    determining pupil localization information using the first 2D image and corresponding 3D depth map;
    refining one or more pupil locations based on the pupil localization information using a convolution with one or more kernels and one or more 2D center-surround filters;
    determining one or more pupil center coordinates; and
    calculating the PD of the subject between centers of each pupil.

2. The method of claim 1, wherein the pupil localization information is determined using a plurality of face mesh landmarks to generate a plurality of face mesh vertices near the center of an eye opening to obtain one or more initial pupil locations on the subject.

3. The method of claim 1, wherein the one or more kernels use a pupil estimate size of approximately 12 mm.

4. The method of claim 1, wherein calculating the PD uses depth map values that correspond to the refined one or more pupil locations in the 2D image.

5. The method of claim 1, wherein calculating the PD is determined by using points on a 3D face mesh that correspond to the centers of each pupil.

6. The method of claim 1, further comprising the steps of:
    performing a correction on the PD calculated using a distance that the first 2D image is taken from the at least one camera.

7. A non-transitory computer readable medium having computer-executable instructions embodied thereon, wherein, when executed by a processor, the computer-executable instructions cause the processor to:
    obtain, from at least one camera, a first 2D image and a corresponding 3D depth map of a face of a subject;
    determine pupil localization information using the first 2D image and corresponding 3D depth map;
    refine one or more pupil locations based on the pupil localization information using a convolution with one or more kernels and one or more 2D center-surround filters;
    determine one or more pupil center coordinates; and
    calculate the PD of the subject between centers of each pupil.

8. The non-transitory computer readable medium of claim 7, wherein the pupil localization information is determined using a plurality of face mesh landmarks to generate a plurality of face mesh vertices near the center of an eye opening to obtain one or more initial pupil locations of the subject.

9. The non-transitory computer readable medium of claim 7, wherein the one or more kernels use a pupil estimate size of approximately 12 mm.

10. The non-transitory computer readable medium of claim 7, wherein calculating the PD uses depth map values that correspond to the refined one or more pupil locations in the 2D image.

11. The non-transitory computer readable medium of claim 7, wherein calculating the PD is determined by using points on a 3D face mesh that correspond to the centers of each pupil.

12. The non-transitory computer readable medium of claim 7, wherein the computer-executable instructions further cause the processor to perform a correction on the PD calculated using a distance that the first 2D image is taken from the at least one camera.

13. A pupillary distance ("PD") system, comprising:
a mobile device, comprising:
at least one camera;
memory storing information associated with images and information obtained from the at least one camera; and
a processor configured to:
obtain, from the at least one camera, a 2D image and a corresponding 3D depth map of a face of a subject;
determine pupil localization information using the 2D image and corresponding 3D depth map;
refine one or more pupil locations based on the pupil localization information using a convolution with one or more kernels and one or more 2D center-surround filters;
determine one or more pupil center coordinates; and
calculate the PD between centers of each pupil of the subject.

14. The PD system of claim 13, wherein the pupil localization is determined using a plurality of face mesh landmarks to generate a plurality of face mesh vertices near the center of an eye opening to obtain one or more initial pupil locations of the subject.

15. The PD system of claim 13, wherein the one or more kernels use a pupil estimate size of approximately 12 mm.

16. The PD system of claim 13, wherein calculating the PD uses depth map values that correspond to the refined one or more pupil locations in the 2D image.

17. The PD system of claim 13, wherein calculating the PD is determined by using points on a 3D face mesh that correspond to the centers of each pupil.

* * * * *